(12) United States Patent
Lee et al.

(10) Patent No.: US 9,750,554 B2
(45) Date of Patent: Sep. 5, 2017

(54) INSTRUMENT FOR EXTRACTING A PIN

(71) Applicant: DEPUY IRELAND UNLIMITED COMPANY, Cork (IE)

(72) Inventors: Jonathan Lee, Dallas, TX (US); Craig Tsukayama, Fort Wayne, IN (US); Duncan Young, Leeds (GB)

(73) Assignee: DEPUY IRELAND UNLIMITED COMPANY (040419/0433), Cork (IE)

( * ) Notice: Subject to any disclaimer, the term of this patent is extended or adjusted under 35 U.S.C. 154(b) by 365 days.

(21) Appl. No.: 14/441,313

(22) PCT Filed: Dec. 23, 2013

(86) PCT No.: PCT/GB2013/053419
§ 371 (c)(1),
(2) Date: May 7, 2015

(87) PCT Pub. No.: WO2014/102541
PCT Pub. Date: Jul. 3, 2014

(65) Prior Publication Data
US 2015/0305793 A1    Oct. 29, 2015

(30) Foreign Application Priority Data
Dec. 28, 2012 (GB) .................................. 1223472.0

(51) Int. Cl.
A61B 17/88 (2006.01)
A61B 17/92 (2006.01)
B25C 11/00 (2006.01)

(52) U.S. Cl.
CPC .......... *A61B 17/92* (2013.01); *A61B 17/8872* (2013.01); *B25C 11/00* (2013.01)

(58) Field of Classification Search
CPC ...... A61B 17/92; A61B 17/8872; B25C 11/00
(Continued)

(56) References Cited

U.S. PATENT DOCUMENTS 4,028,790 A   6/1977   Dupuis
4,627,420 A   12/1986  Katz
(Continued)

FOREIGN PATENT DOCUMENTS

CN    2751757 Y    1/2006
CN   200945186 Y   9/2007
(Continued)

OTHER PUBLICATIONS

PCT Written Opinion, 8 Pages.
(Continued)

*Primary Examiner* — Christian Sevilla

(57) ABSTRACT

An instrument for extracting a pin from a substrate, such as a bone mass, which comprises a first lever arm with a body part having a channel in which a free end of a pin can be received, a second lever arm which can pivot relative to the first lever arm, a gripping member within the body part by which the pin can be gripped to retain the pin in the channel, and a terminating member mounted on the body part having an end face and two side walls which extend along opposite sides of the body part. The terminating member has a slot provided in a portion of the end face and which extends along a portion of at least one of the two side walls configured to guide the free end of the pin into the instrument prior to being received into the channel.

10 Claims, 11 Drawing Sheets

(58) Field of Classification Search
USPC .................................................. 254/18; 81/44
See application file for complete search history.

(56) References Cited

U.S. PATENT DOCUMENTS

| | | | |
|---|---|---|---|
| 6,039,313 | A | 3/2000 | Baculy |
| 6,066,143 | A | 5/2000 | Lane |
| 6,673,078 | B1 | 1/2004 | Muncie |
| 7,189,243 | B1 | 3/2007 | Seelig et al. |
| 7,341,587 | B2 | 3/2008 | Molz, IV |
| 7,993,349 | B2 | 8/2011 | Hearn et al. |
| 2010/0087831 | A1 | 4/2010 | Marx |
| 2010/0234851 | A1 | 9/2010 | Graves |

FOREIGN PATENT DOCUMENTS

| | | | | |
|---|---|---|---|---|
| CN | 202446247 U | 9/2012 | | |
| EP | 2043538 | 4/2009 | | |
| JP | 30-7300 Y | 5/1955 | | |
| JP | 40-32637 Y | 11/1965 | | |
| TW | FR 2833200 A3 * | 6/2003 | ............ | B25B 27/00 |
| WO | WO 96/28103 A1 | 9/1996 | | |
| WO | WO 97/00648 A1 | 1/1997 | | |

OTHER PUBLICATIONS

International Search Report for PCT App. No. PCT GB2007002498 dated Sep. 21, 2007, 3 Pages.
UK Search Report dated Nov. 23, 2006, 1 Page.
UK Search Report Regarding App. No. GB1223472.0 dated Apr. 4, 2013.
International Search Report for PCT GB2013053419 dated Mar. 14, 2014, 4 Pages.
PCT Written Opinion for PCT GB2013053419, 5 Pages.
Chinese Search Report for Corresponding Chinese Application No. 201380068354.3, dated Jan. 13, 2017, 3 Pages.
English Translation of Japanese Notification of Reasons for Refusal for Corresponding Japanese Patent Application No. 2009-521326, dated Jun. 22, 2012, 3 Pages.

* cited by examiner

INSTRUMENT FOR EXTRACTING A PIN

CROSS REFERENCE TO RELATED APPLICATION

This application is a National Stage 35 U.S.C. 371 of International Patent Application PCT/GB2013/053419 filed Dec. 23, 2013, claiming priority to United Kingdom applications GB1223472.0, filed Dec. 28, 2012 (now abandoned).

BACKGROUND OF THE INVENTION

This invention relates to an instrument for extracting a pin.

Removal of a fastening pin from a substrate requires that the pin is gripped securely so that a removal force is transmitted reliably to the pin. Gripping a pin which has an enlarged head can be achieved reliably by engaging the head of the pin. However, when a pin does not have an enlarged head, or when it is necessary to grip the pin other than at the end where it has an enlarged head, gripping the pin requires secure engagement with the side wall of the pin.

This problem is encountered in orthopaedic surgery procedures, for example when a pin is used to mark a location on a bone, or to fasten an instrument such as a cutting guide (for example which defines a surface for a cutting step using a saw, or which defines bores for a drilling or reaming step) to a bone. The pin has to be removed from the bone after the steps involving the pin and the instruments which have been fastened to the bone by means of the pin have been completed.

EP-B-2043538 discloses an instrument for extracting a pin from a substrate. The instrument has an aperture at its tip into which the pin is received prior to extraction.

To insert the pin easily through the aperture, the instrument needs to be placed at the correct position and angle by the surgeon. However, when doing this, the instrument blocks the surgeon's view of the pin and the aperture. As such, the surgeon performs this operation 'blind'. This can make it very difficult for the surgeon to get the instrument at the right position and angle to ensure that the pin is received through the aperture correctly and may require several attempts.

BRIEF SUMMARY OF THE INVENTION

According to an aspect of the present invention, there is provided an instrument for extracting a pin from a substrate, the instrument comprising: a first lever arm with a body part having a channel in which a free end of a pin can be received, a second lever arm which can pivot relative to the first lever arm, a gripping member within the body part by which the pin can be gripped to retain the pin in the channel, and a terminating member mounted on the body part having an end face and two side walls which extend along opposite sides of the body part, wherein the terminating member has a slot provided in a portion of the end face and extending along a portion of at least one of the two side walls configured to guide the free end of the pin into the instrument prior to being received into the channel.

The provision of a slot on the side as well as the front enables a user, such as a surgeon, to manoeuvre the pin to be extracted into the channel either through the front of the extraction instrument or at the side. This enhances the flexibility of the instrument and means that the user is less prone to misaligning the pin within the extraction instrument.

The provision of the slot passing along at least a portion of the side of the instrument also provides tactile feedback to the user which enhances the ease of use of the instrument to remove pins. Engagement of the pin head in the slot provides some tactile feedback during handling of the device by the user. The user can feel, sometimes see, and in some circumstances may be able to hear, the pin going into the slot. By virtue of the arrangement of the slot and the user's instinctive application of force to keep the pin in the slot, the user is able to reduce the degrees of freedom of movement of the pin relative to the instrument one at a time. This is in contrast to the instrument mentioned above, in which the users has to float the pin around on the front face of the instrument, and align all of the degrees of freedom at the same time before they can get introduce the pin into the instrument.

The slot may be provided down a portion of the side wall, or a substantial portion of the side wall or along the entire length of the side wall. The slot may extend for at least 10 mm, 20 mm, 30 mm, 40 mm, or 50 mm.

The slot may have an open form with no bottom, so that the pin can pass in through the side of the instrument.

The slot may be in the form of a trench and have a closed bottom. The slot may include a guide surface to guide the pin during side entry.

The slot may also include a stop surface to limit lateral movement of the pin along the front face of the terminating member and to facilitate entry of the pin into the instrument during forward entry.

The gripping member may be connected to the first and second levers such that relative movement of the first and second levers causes the gripping member to grip the pin.

The instrument may be made of biocompatible materials.

The first lever arm may be inclined with respect to the body part.

The provision of an inclined first lever arm provides for enhanced visibility to the user as the lever arm is not in the line of vision: thus assisting in maneuvering the pin into the instrument. Further, the provision of the inclined lever arm provides better ergonomics as the wrist angle adopted when pumping the lever is more favourable for the surgeon and less likely to lead to injury. Also, the inclined lever arm has the added advantage that when the pin exits the back of the slot or hole, the pin is easy to see and catch. In contrast, in the embodiment in which the lever arms are generally aligned with the body, the pin can pop out between the two handle into the middle of the surgeon's hand.

The first lever arm may subtend an obtuse angle to the body part and the second lever arm may subtend an acute angle to the body part.

The first and second lever arms may be biased in an open position. The biasing member may be a spring or it may be a pair of leaf spring components.

The body part may include a pair of recesses for receiving the first and second side walls therein.

The instrument can comprise entirely a plurality of interlocking parts. The interlocking parts can be assembled into the instrument and no any ancillary parts are needed in order to assemble the instrument. Hence, no ancillary fixings, securing or attachment means (such as screws, bolts, adhesives, welding or similar) need to be used to assemble the instrument into its usable form.

The first lever arm can include a protuberance toward a leading end and/or a trailing end of a handle part. Additionally or alternatively, the second lever arm can include a protuberance toward a leading end and/or a trailing end of a handle part.

The first and/or the second lever arm each include protuberances toward a leading end and/or a trailing end of a handle part of each lever arm.

BRIEF DESCRIPTION OF THE DRAWINGS

Embodiments of the invention will now be described by way of example with reference to the accompanying drawings, in which.

DETAILED DESCRIPTION OF THE INVENTION

Figure 1:
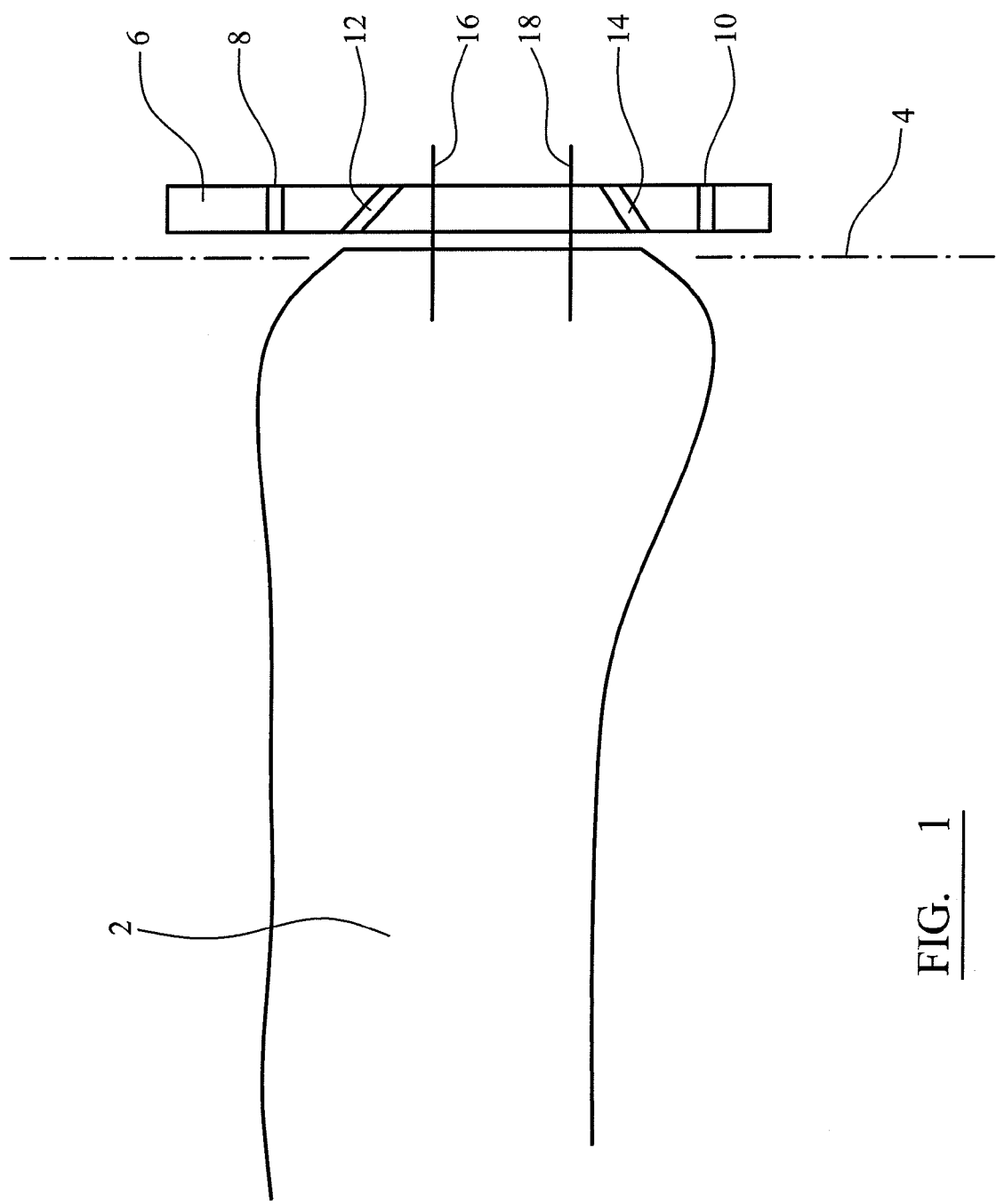
FIG. 1 is a side view of the distal end of a femur during a surgical procedure to implant a knee prosthesis, with a cutting guide block located on the end of the femur by means of two fixation pins.

Referring to the drawings, FIG. 1 shows schematically the distal portion of a femur 2 which is being prepared for implantation of the femoral component of a knee joint prosthesis. An initial distal cut has been performed on the femur 2 on a resection plane 4. A cutting block 6 is in place against the resected femur 2. The cutting block 6 has slots 8, 10, 12, 14 to define the planes of the anterior cut, the posterior cut, the anterior chamfer cut, and the posterior chamfer cut respectively. The cutting block 6 is held in place by means of two fixation pins 16, 18 which pass through respective bores in the cutting block 6. The appropriate location of the cutting block 6 on the resected femur 2 can be located using existing techniques, for example with reference to an intra-medullary alignment rod.

After performing the cutting steps using the cutting block 6, the cutting block 6 can be removed from the femur 2 to allow access to the resected femur 2 for subsequent stages in the procedure. When the fixation pins 16, 18 are parallel, and do not have enlarged heads at their free ends, the cutting block 6 can be removed from the resected femur by sliding it over the pins. The fixation pins 16, 18 therefore need to be removed.

The present invention addresses the removal of the fixation pins 16, 18.

Figure 2:
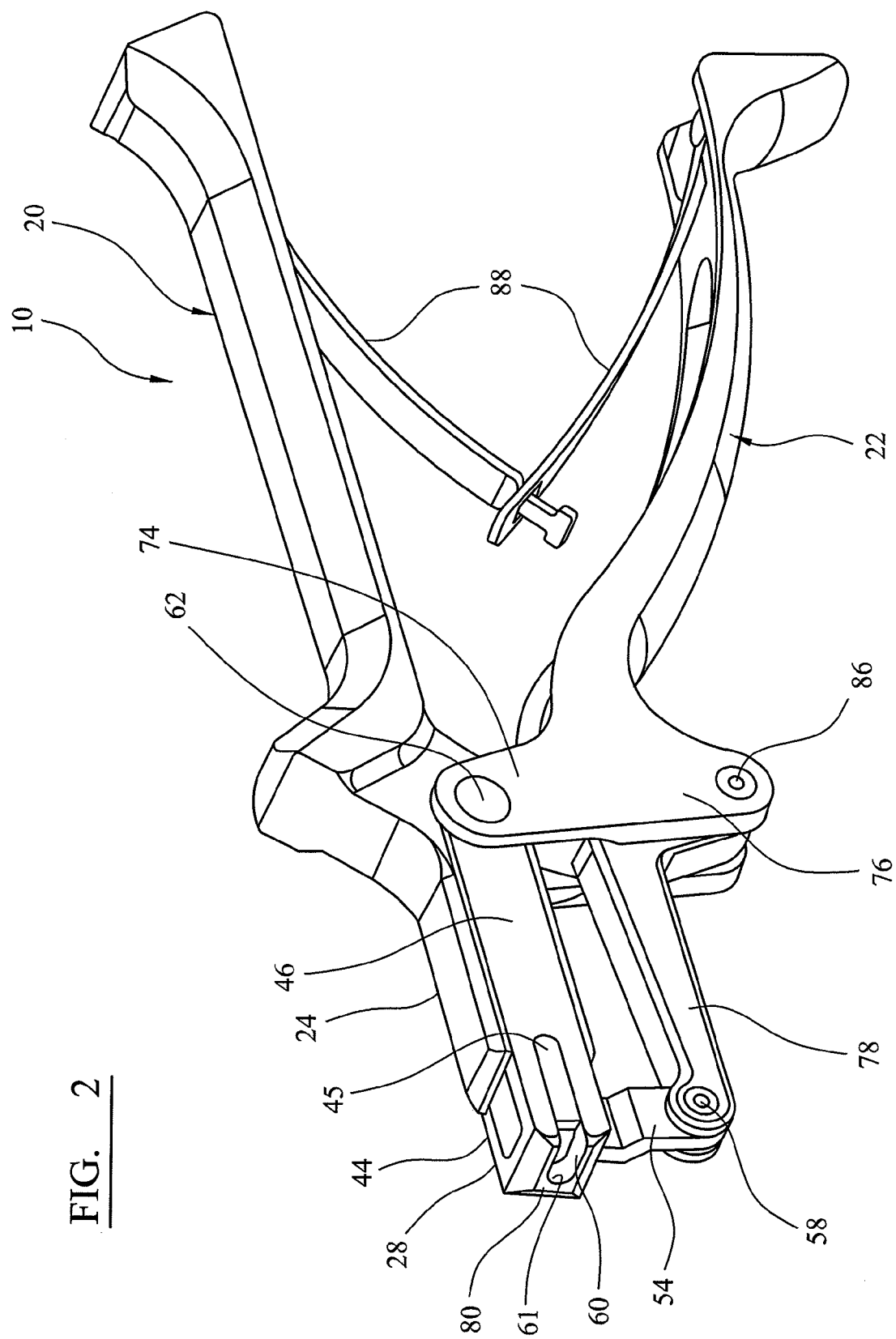
FIG. 2 is a perspective view of an instrument for extracting a fixation pin according to the present invention.

FIG. 2 shows an instrument 10 for extracting fixation pins according to the present invention. The instrument 10 comprises a first lever arm 20 and a second lever arm 22. The second lever arm 22 is connected indirectly by means of linkages (described in more detail below) to the first lever arm 20 so that the second lever arm 22 can pivot relative to the first lever arm 20.

The first lever arm 20 includes a body part 24 having a circular cavity 26 and a longitudinal cavity 38 formed in it.

The first lever arm 20 has a handle portion 30 at an end opposite to the body part 24. The second lever arm 22 comprises a curved handle portion 32 by which it can be gripped, and which is located opposite to the handle portion 30 of the first lever arm when the instrument 10 is assembled so that the two handle portion 30, 32 can be gripped by an operator in the palm of their handed and gripped between thumb and fingers to squeeze them together. The dimensions of the handle portions and their shapes (the fact that the two handle portions are angled relative to one another and that the second handle portion 32 has a curved form) have been selected to optimise the grasp distance to be accessible and comfortable to a wide range of users' hand sizes across the distances needed for them to give a good powerful grasp. Also, protuberances or flanges are provided at the leading and trailing ends of each handle portion to assist with pushing and pulling when users' gloves are slippery.

The body part 24 is substantially rectangular in cross-section and includes a tip portion 34 at an end remote from the handle portion 30.

The longitudinal cavity 38 is provided in a main section 36 of the body part 24. The main section 36 has the tip portion 34 formed at one end and the handle portion 30 at its other end. The main section 36 of the body part 24 has two substantially parallel, outwardly-facing recesses 40, 42 on opposing faces of the main section 36 running along substantially the length of the main section 36 and arranged to receive respective first and second side walls 44, 46 of a terminating member 28.

The tip portion 34 has a cylindrical cavity 26 and a first circular aperture 92 in the forward face 48 thereof. The circular aperture 92 extends into the circular cavity 26. A second circular aperture 52 extends from the circular cavity 26 into the longitudinal cavity 38.

The terminating member 28 terminates the body part 24 and serves to connect the first lever arm 20 and second lever arm 22 via linkages referred to above and to facilitate removal of the fixation pin 16. The terminating member 28 comprises an end face 80 with the first and second side walls 44, 46.

The terminating member 28 is arranged for slidable movement relative to the body part 24 with the first and second side walls 44, 46 being receivable in the respective recesses 40, 42 to facilitate the relative movement between the terminating member 28 and the body part 24.

The first and second side walls 44, 46 of the terminating member 28 extend generally parallel to one another, and are interconnected at one end by means of the end face 80.

Figure 7:
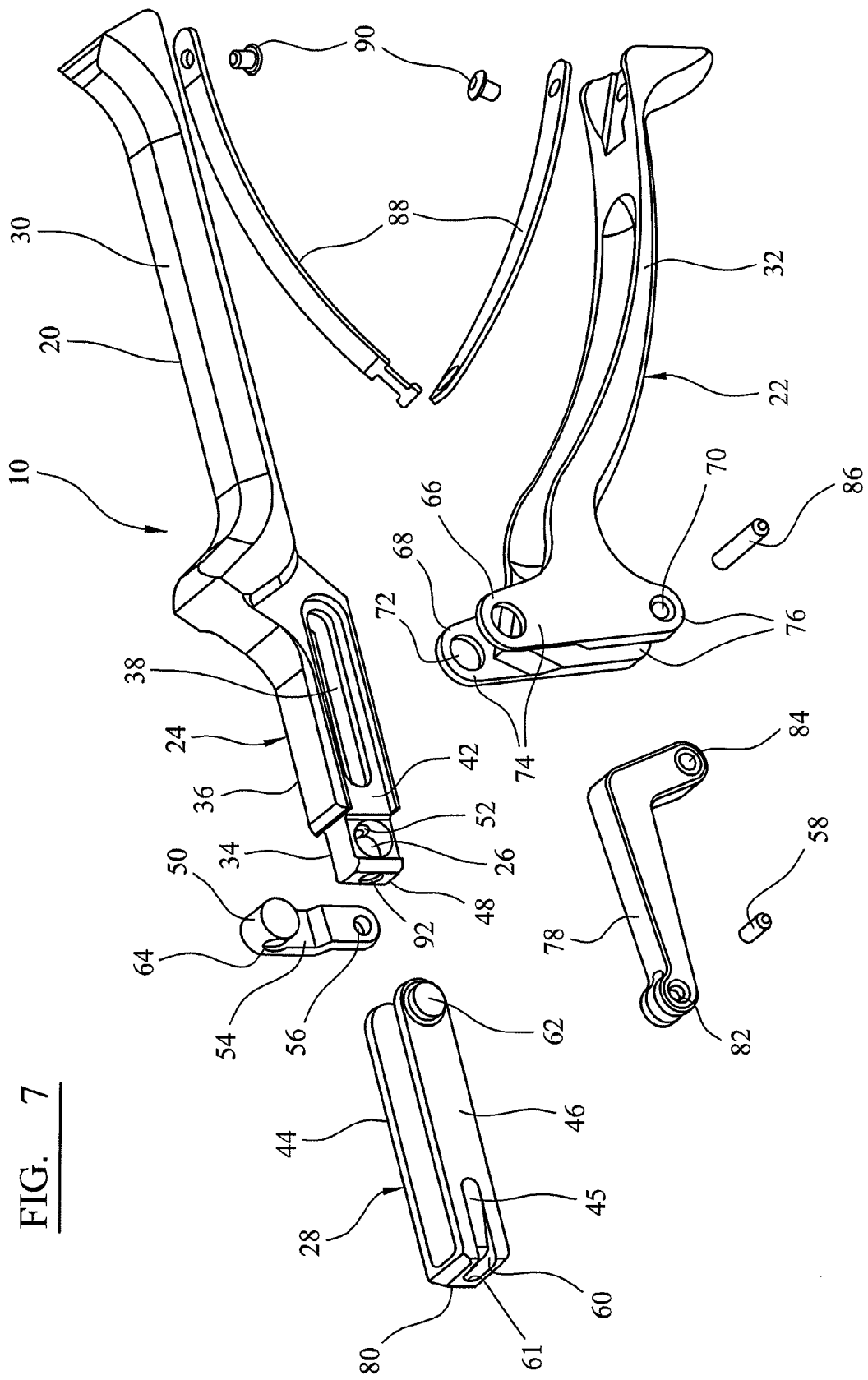
FIG. 7 is an exploded view of the instrument of FIG. 2.

The end face 80 and a portion of one of the side walls 44, 46 has a single slot 60 provided therein. As illustrated in FIG. 7, the slot 60 extends from a central portion of the end face 80 towards the second wall 46 and then continues in a substantially orthogonal direction along a forward portion of the second wall 46. The slot 60 can extend down either side wall 44, 46 of the terminating member 28.

At the forward portion of the second wall 46, contiguous with the slot 60, an inclined, recessed guide surface 45 is formed that slopes inwardly of the terminating member 28. The guide surface 45 terminates adjacent the forward face 48 of the tip portion 34 of the main section 36.

An outwardly facing spigot 62 is provided at the free end of each of the first and second side walls 44, 46. The first and second side walls 44, 46 are dimensioned so that they can slide in the recesses 40, 42 of the main section 36 of the body part 24.

Figure 8:
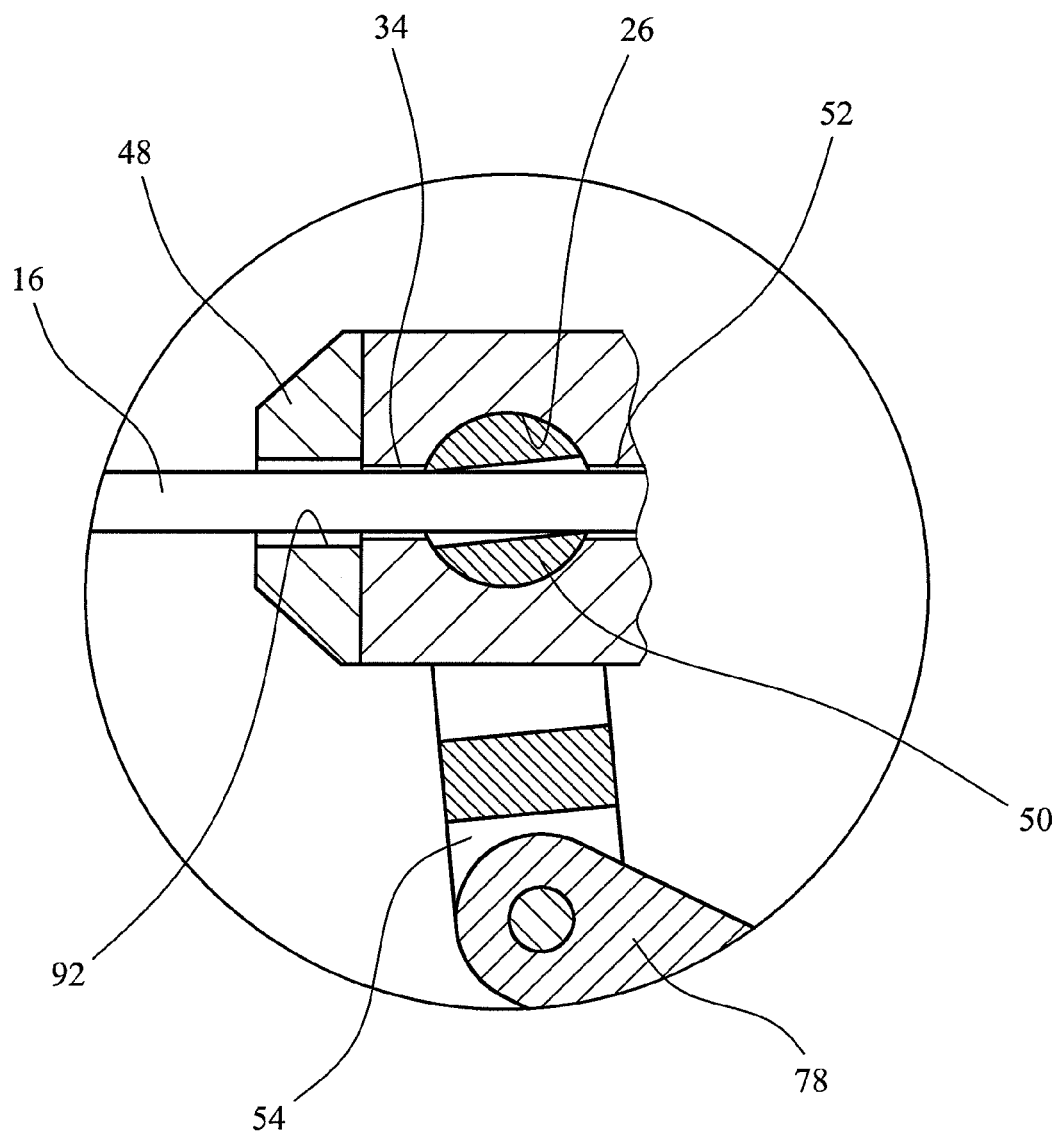
FIG. 8 is a schematic cross-section of the end of the instrument of FIG. 2 illustrating the operation of the jaw component.

A gripping member in the form of a jaw component 50 is located in the circular cavity 26, and can be rotated within the circular cavity 26 to cause a fixation pin 16, the end of which is inserted into the circular cavity 26, to be gripped when the second lever arm 22 is moved relative to the first lever arm 20. This is illustrated in FIG. 8.

The jaw component 50 has a dog-leg shaped control arm 54 which has an aperture 56 provided at its free end.

Figure 3:
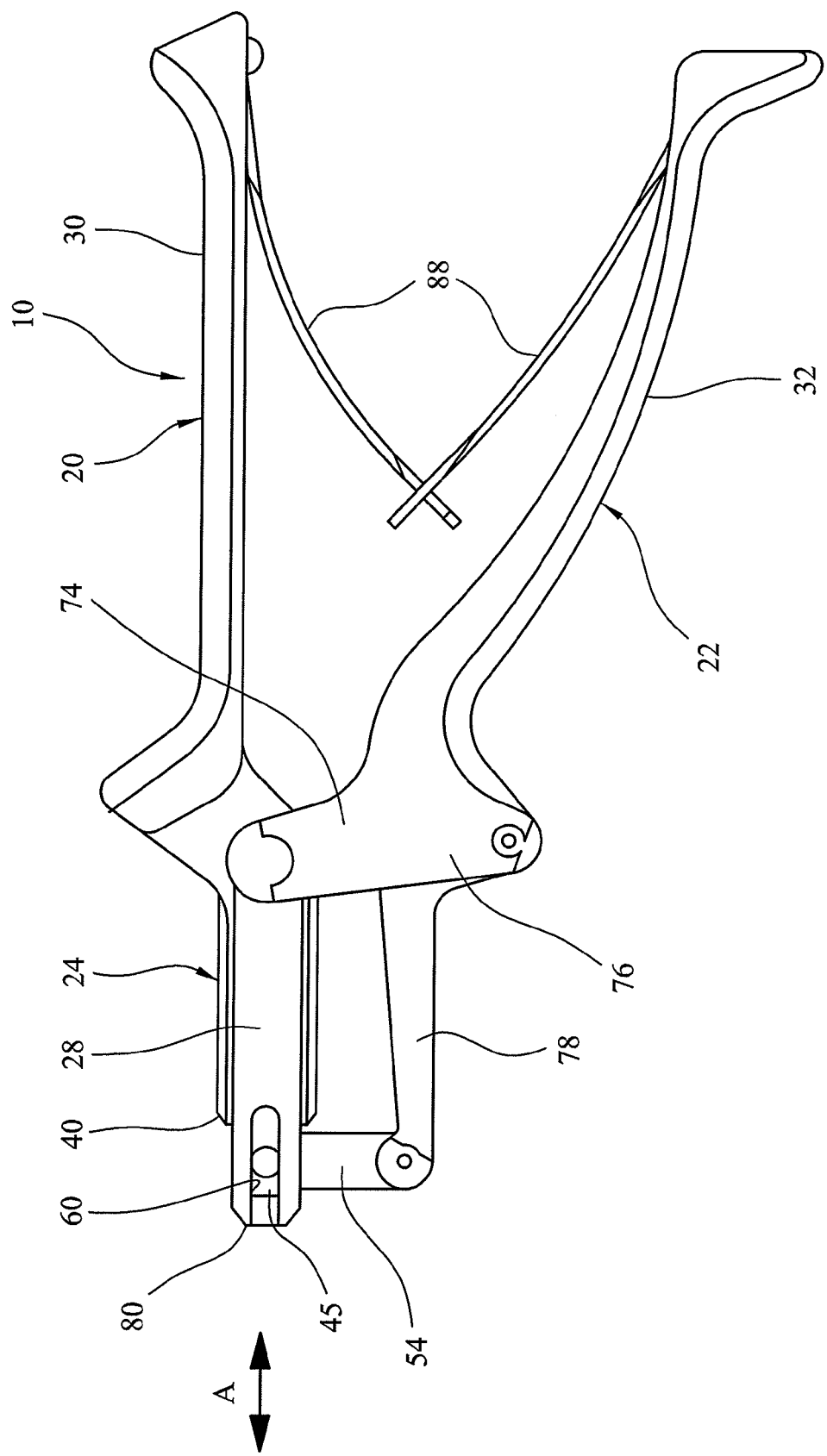
FIG. 3 is a side view of the instrument of FIG. 2.
Figure 4:
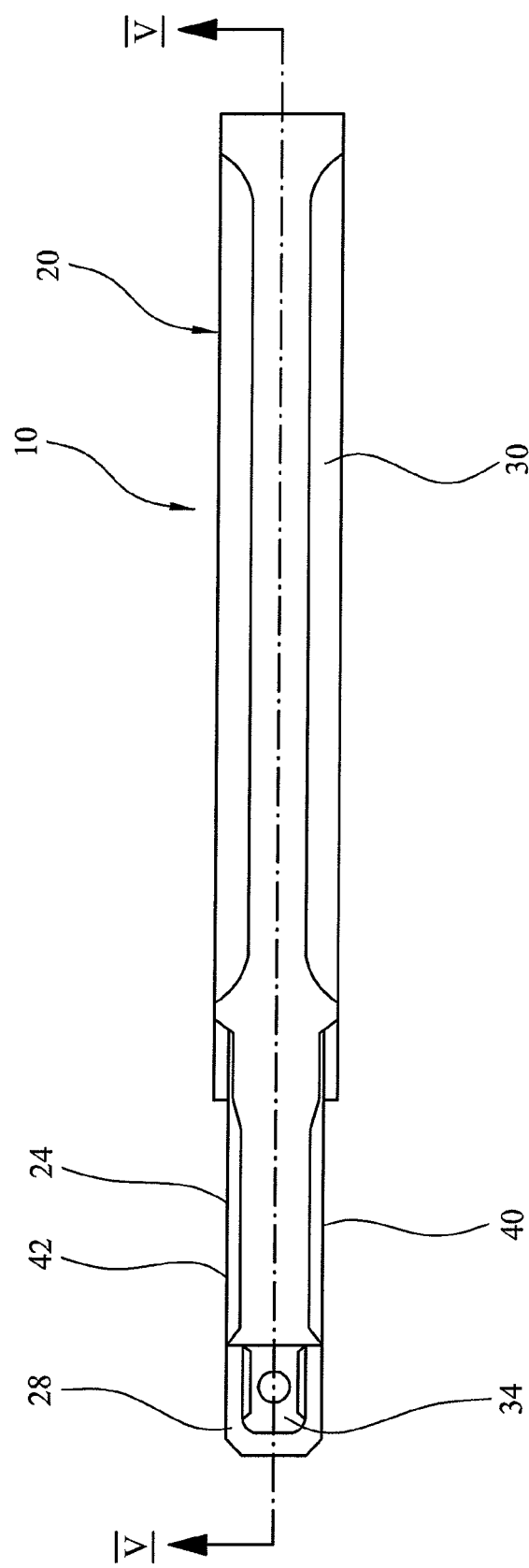
FIG. 4 is a plan view of the instrument of FIG. 3 in the direction of arrow IV in FIG. 6.

The terminating member 28 can slide relative to the body part 24 of the first lever arm 20, in a direction towards the substrate from which the pin 16 is to be extracted, as illustrated by the arrow A in FIG. 3. In the context of the application described above, the substrate can be the femur 2.

Relative movement between the first and second lever arms 20, 22 initially causes the jaw component 50 to be actuated from an unlocked position to a locked position so that the inserted pin 16 is gripped by the jaw component 50. Continued movement of the second lever arm 22 relative to the first lever arm 20 causes the terminating member 28 to slide towards the substrate and away from the body part 24, so that the inserted pin 16 which is gripped by the jaw component 50 is displaced relative to the substrate.

The circular jaw component 50 is a close fit in the circular cavity 26, and is dimensioned so that it can rotate without excessive play in contact within the circular cavity 26.

Figure 5:
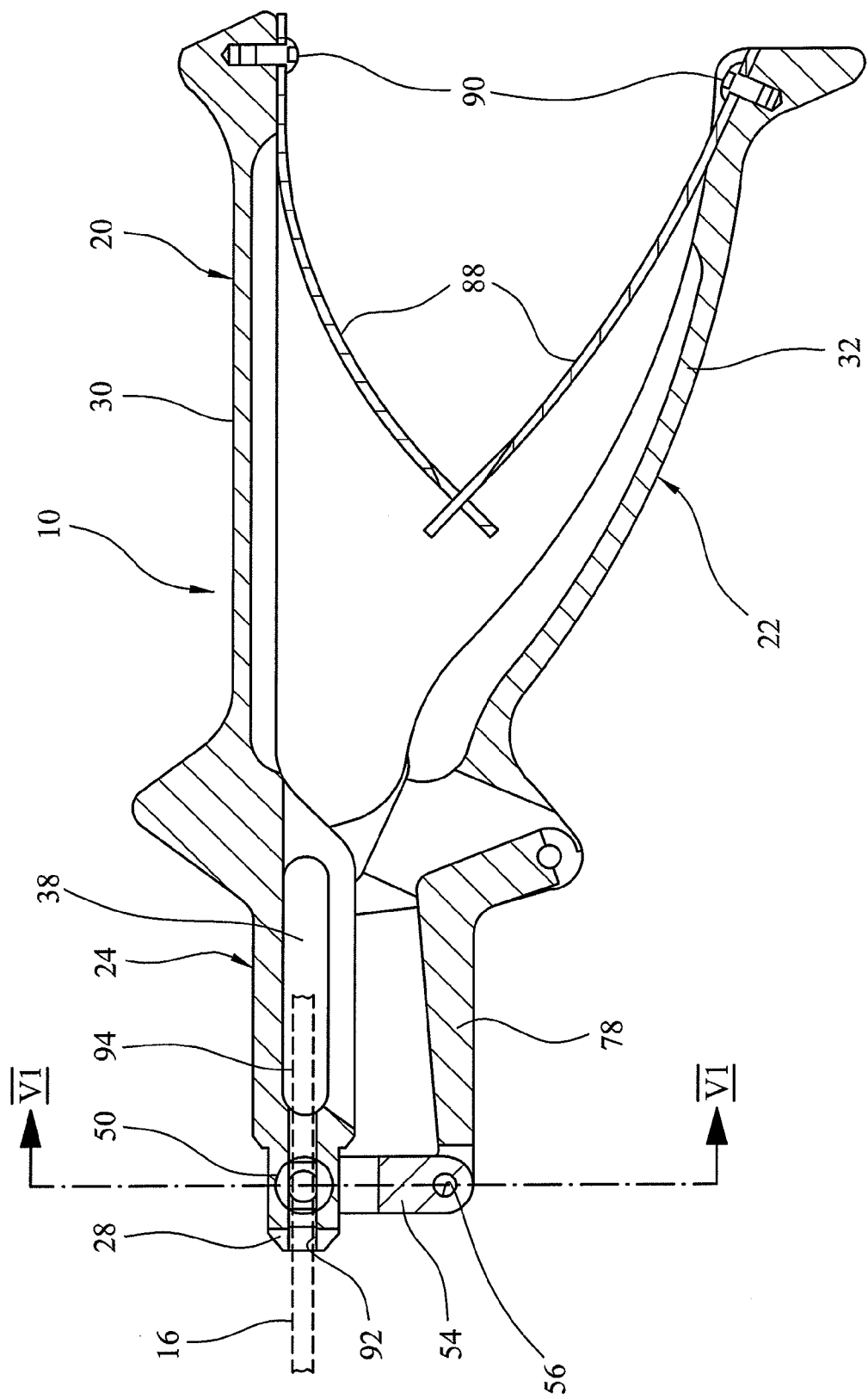
FIG. 5 is side cross-section along the line V-V of FIG. 4.

The jaw component 50 has a bore 64 extending through it. The bore 64 in the jaw component 50 has the same cross-sectional size and profile as the first circular aperture 92 in the front face 48 of the tip portion 34 and the second circular aperture 52 extending from the circular cavity 26 into the longitudinal cavity 38. When the jaw component 50 is in place in the circular cavity 26, the bore 64 is able to rotate to align with the first and second circular apertures 92, 52 so as to be also co-linear therewith and to define a channel 94 that extends from the front face 48 of the first lever arm 20, through the jaw component 50, and through into the longitudinal cavity 38, and into which the free end of the pin 16 can be received. This is illustrated in FIG. 5.

The slot 60 is formed in the terminating member 28 to be in alignment with the bore 64 and the first and second circular apertures 92, 52 i.e. with the channel 94, so that the first and second circular apertures 92, 52, the bore 64 and the slot 60 can therefore be aligned to receive the end of the fixation pin 16.

Leaf spring components 88 are provided for fastening to the first and second lever arms 20, 22. They are connected to the first and second lever arms 20, 22 by means of fixation screws 90. The leaf spring components 88 bias the first and second lever arms 20, 22 in the open position.

In this position, the rotational orientation of the jaw component 50 is such that the bore 64 can be aligned with the first and second circular apertures 92, 52 as described above.

The second lever arm 22 terminates with a pair of substantially parallel connection plates 66, 68 for linkedly connecting the second lever arm 22 to the first lever arm 20. Each connection plate 66, 68 comprises first and second extensions 74, 76 for coupling the second lever arm 22 to the terminating member 28 and control arm 54 respectively.

Each of the connection plates 66, 68 has one of a first pair of aligned through holes 72 on the first extension 74. The through holes 72 can receive the outwardly facing spigots 62 on the terminating member 28, so that the second lever arm 22 is connected to the terminating member 28 but can pivot relative to it.

The second lever arm 22 has a second pair of aligned through holes 70: one on each of the second extension 76.

The instrument 10 includes an L-shaped linkage arm 78 to interconnect the control arm 54 at its free end with the second lever arm 22. The linkage arm 78 has through holes 82, 84 at its opposite ends, for receiving respective axles 58, 86 that are welded in position on the outside.

The instrument 10 is operated as follows.

The fixation pin 16 is inserted into the instrument 10 either forward through the slot 60 in the end face 80 of the terminating member 28, or initially from the side of the instrument 10 utilising the section of the slot 60 that extends along the forward portion of the first or second wall 44, 46. The end 61 of the slot 60 provides a stop surface that limits lateral travel of the fixation pin 16 in the slot 60 on the end face 80 to assist in guiding the fixation pin 16 into the first circular aperture 92.

When inserting the fixation pin 16 from the side, the fixation pin 16 will engage the guide surface 45 and is guided by the guide surface 45 towards the forward face 48 of the tip portion 34 so that it aligns with the first circular aperture 92.

The fixation pin 16 may therefore be inserted through the slot 60 from either the front or side of the instrument 10, and then be received into the channel 94 formed by the first and second circular apertures 92, 52, the bore 64 and the longitudinal cavity 38.

Figure 6:
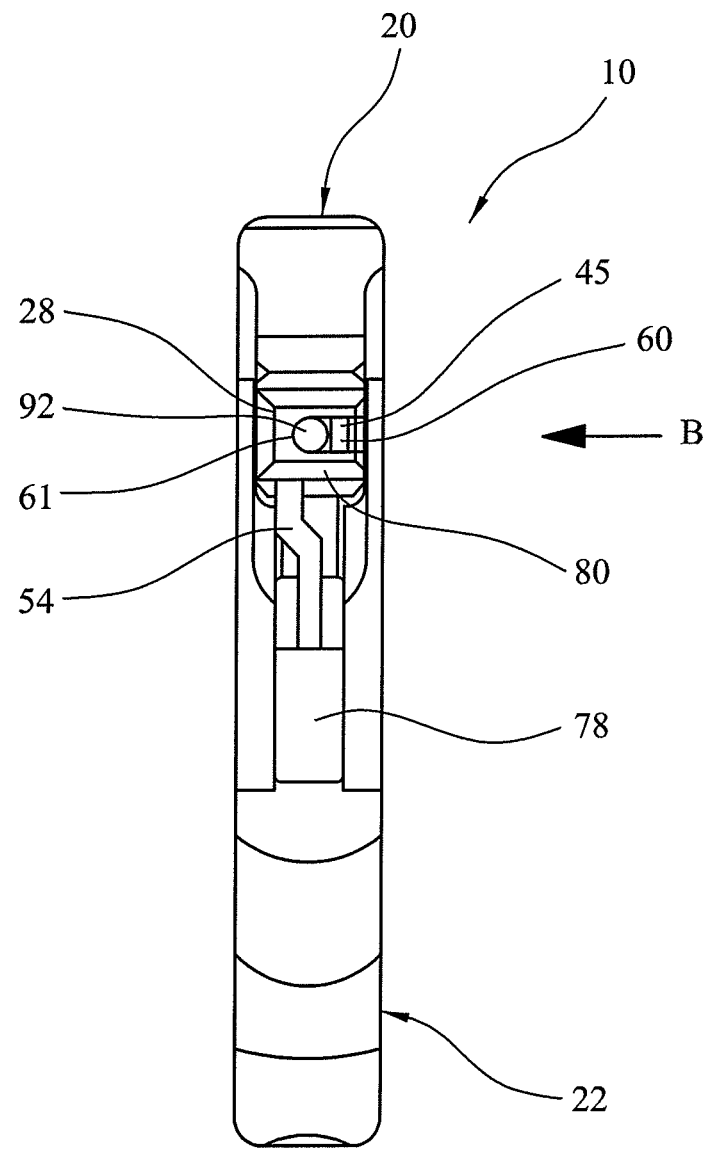
FIG. 6 is front cross-section along the line VI-VI of FIG. 5.

Thus, the surgeon who is operating the instrument 10 is able to manoeuvre the fixation pin 16 into the bore 64 by either a directly forward movement or by a lateral and then forwards movement. The arrow B in FIG. 6 shows the direction of sideways insertion.

Squeezing the first and second lever arms 20, 22 together from the open position initially causes the second lever arm 22 to pivot about the through holes 72 and spigots 62 by which the second lever arm 22 is connected to the terminating member 28. The action of the linkage arm 78 causes the lever arm 54 to be drawn back away from the substrate from which the fixation pin 16 is to be extracted. This, in turn, causes the jaw component 50 to rotate within the circular cavity 26. As the jaw component 50 rotates within the circular cavity 26, portions of the inner surfaces at the ends of the bore 64 in the jaw component 50 impart a shearing action to the fixation pin 16, as a result of applying a localised bending force to the pin. This causes the fixation pin 16 to be gripped within the instrument 10, resisting sliding of the fixation pin 16 in and out of the instrument 100. This is illustrated schematically in FIG. 8.

Continued squeezing together of the first and second lever arms 20, 22 causes the second lever arm 22 to pivot about the through holes 70 at which it is connected to the linkage arm 78 and the control arm 54. The control arm 54 tends to move very little at this stage, subject only to deformation of the fixation pin 16 as a result of further rotation of the jaw component 50 within the circular cavity 26. Accordingly, squeezing together of the first and second lever arms 20, 22 causes the terminating member 28 to be thrust forward relative to the body part 24, by virtue of the connection between the second lever arm 22 and the terminating member 28 at the through holes 72 in the second lever arm 22 with the spigots 62. It will be appreciated that movement of the terminating member 28 will result in some pivotal movement of the linkage arm 74 about its connection to the control arm 54, so that the through holes 70 at which the linkage arm 78 is connected to the second lever arm 22 will tend to move slightly relative to the first lever arm 20.

The result of the continued squeezing together of the first and second lever arms 20, 22 and consequential movement of the terminating member 28 pushing against the bone will cause the fixation pin 16 to be extracted at least partially from the bone or other substrate. Partial extraction using the instruments of the present invention will often be sufficient to loosen the fixation pin 16 so that it can then be slid out of the substrate completely. If the fixation pin 16 has not been loosened sufficiently to enable it to be extracted completely, other than with the application of significant pulling force, the first and second lever arms can be opened, and, while the end face 80 remains in contact with the bone, the rest of the instrument can then be slid along the fixation pin 16. The first and second lever arms 20, 22 can then be squeezed together to repeat the sequence which has been described above.

Figure 9:
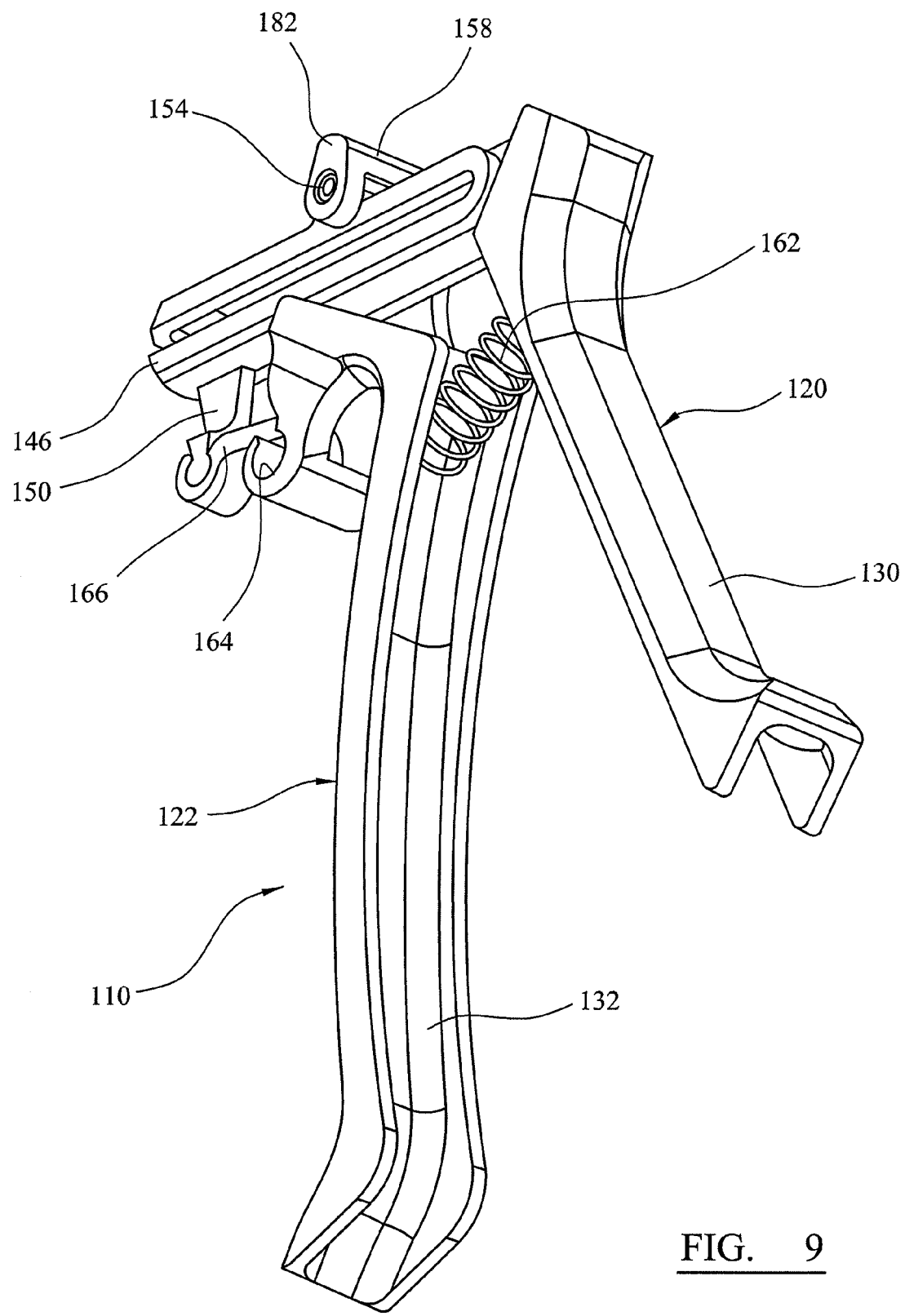
FIG. 9 is a perspective view of an instrument in accordance with a second embodiment of the invention.
Figure 10:
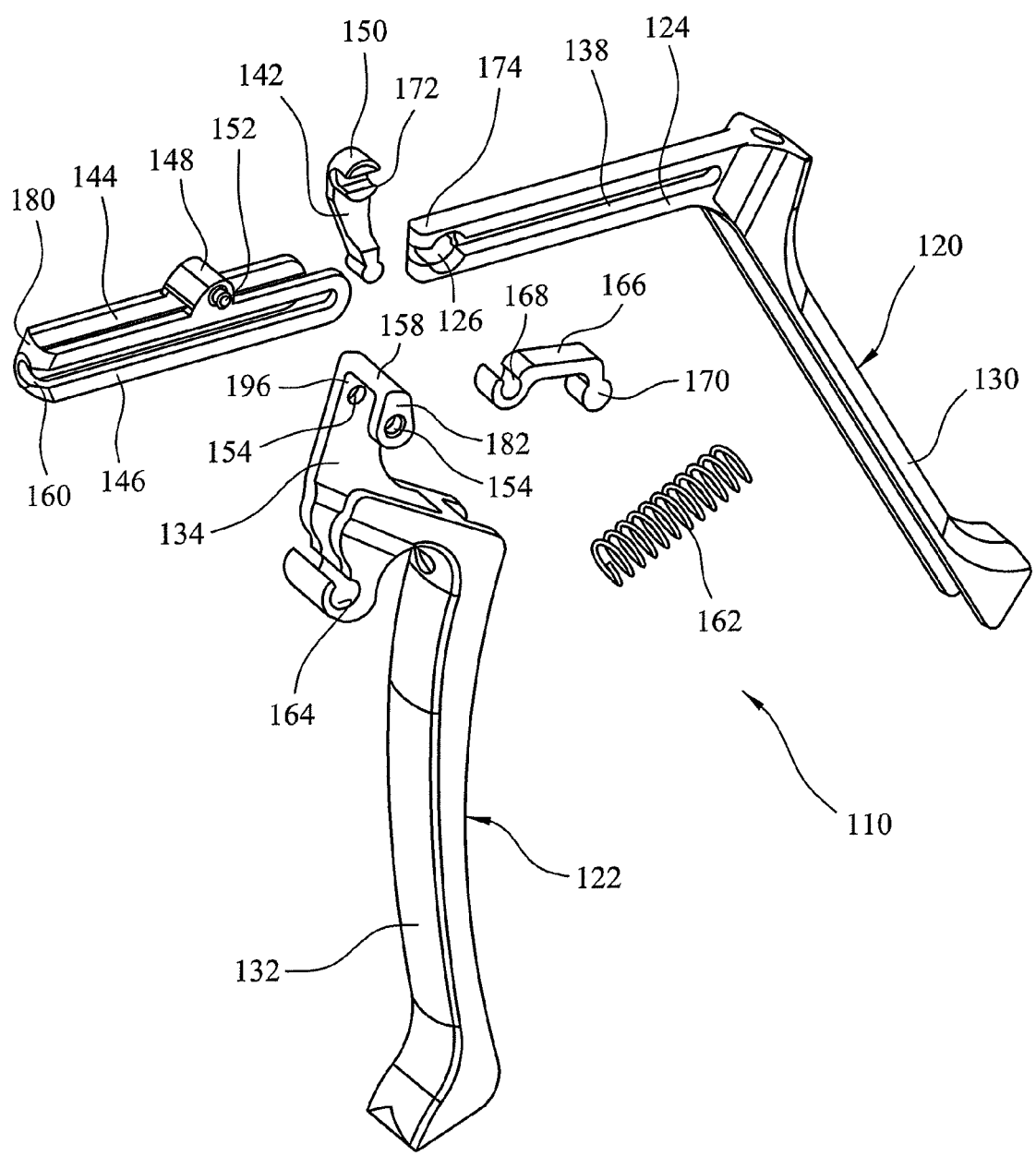
FIG. 10 is an exploded view of the instrument of FIG. 9.
Figure 11:
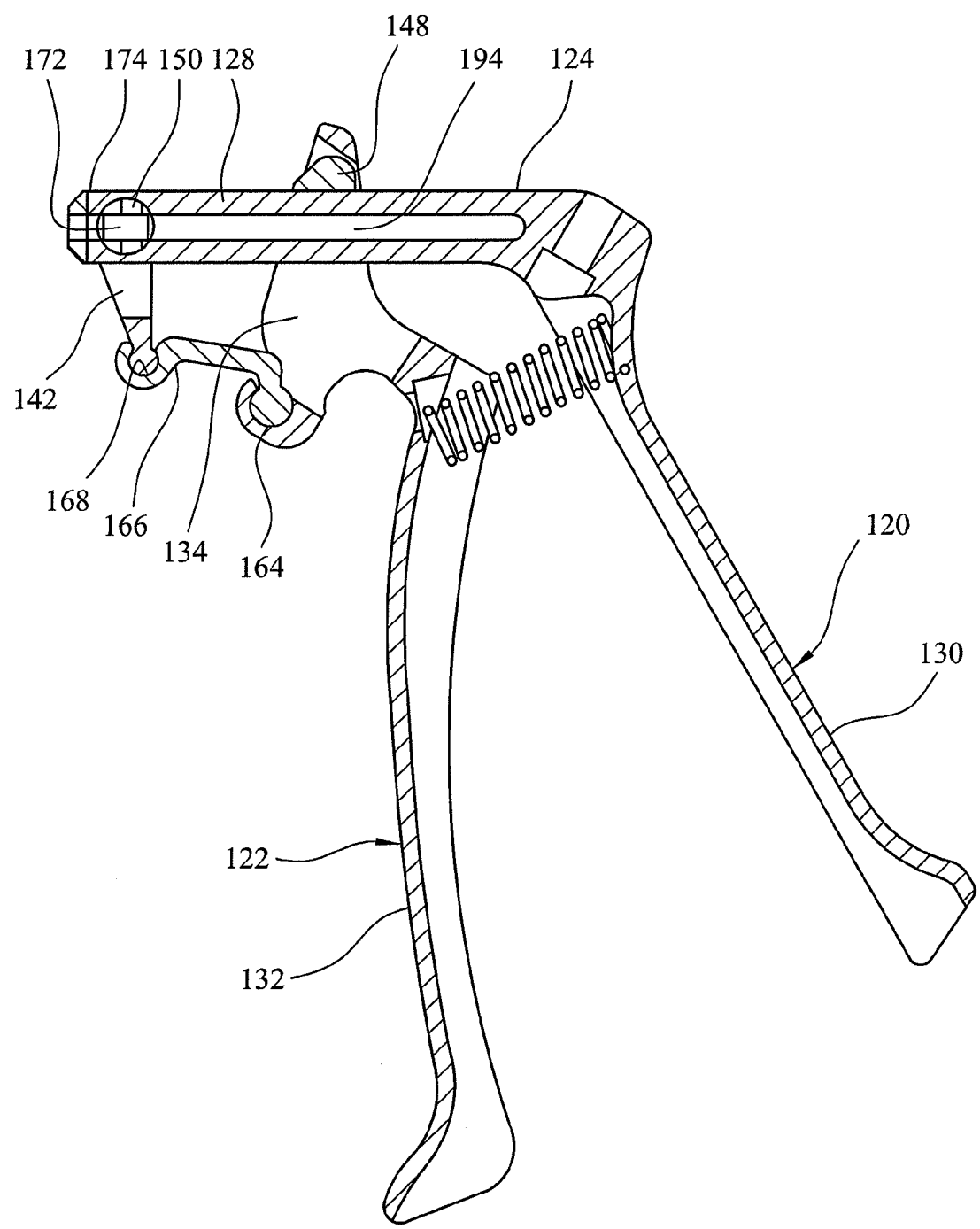
FIG. 11 is a lateral cross-section of the instrument of FIG. 9.

A second embodiment of the invention is described with reference to FIGS. 9 to 11.

An extraction instrument 110 includes a first lever arm 120 and a second lever arm 122. The second lever arm 122 is connected indirectly by means of linkages to the first lever arm 120 so that the second lever arm 22 can pivot relative to the first lever arm 20.

The first lever arm 120 includes an elongate body part 124 and a handle portion 130. The elongate body part 124 has a circular cavity 126 extending widthwise across the elongate body part 124 towards the distal end 174 of the elongate body part 124 remote from the handle portion 130. The elongate body part 124 also includes an elongate cavity 138 formed therein extending from the distal end 174 of the elongate body part 124 through a substantial portion of its length. The circular cavity 126 is contiguous with and opens into the longitudinal cavity 138.

The second lever arm 122 comprises a curved handle portion 132 by which it can be gripped, and which is located opposite to the handle portion 130 of the first lever arm 120 when the instrument 110 is assembled so that the two handle portion 130, 132 can be gripped by an operator in the palm of their handed and gripped between thumb and fingers to squeeze them together.

The dimensions of the handle portions and their shapes (the fact that the two handle portions are angled relative to one another and that both have a curved form) have been selected to optimise the grasp distance to be accessible and comfortable to a wide range of users' hand sizes across the distances needed for them to give a good powerful grasp. Also, protuberances or flanges are provided at the leading and trailing ends of each handle portion to assist with pushing and pulling when users' gloves are slippery.

The first and second lever arms 120, 122 are connected by means of a compression spring 162 which biases the first and second lever arms 120, 122 to an open position.

The first lever arm 120 is inclined with respect to the elongate body part 124. In the embodiment described herein, the first lever arm subtends an obtuse angle with the elongate body part 124. The second lever arm 122 also subtends an acute angle with the elongate body part 124. With this arrangement, the view of the main body part 124 is not obscured by an operator of the instrument 110.

The second lever arm 122 includes a linkage and connection arrangement for connecting the second lever arm 122 to the body part 124 via a terminating member 128 and jaw component 150 as will be described in further detail below.

The terminating member 128 comprises first and second side walls 144, 146 extending substantially generally parallel to one another, and interconnected at one end by means of an end face 180. The pair of first and second side walls 144, 146 define a recess 156 into which the elongate body part 124 is received.

A projection 148 is provided on the upper side of the terminating member 128, extending between the first and second side wall 144, 146 and about half way down the terminating member 128. A pair of co-linear spigots 152 on opposing outwardly facing faces of the projection 148 is provided for connecting to respective aligned holes 154 provide in a linkage and connection arrangement of the second lever arm 122.

The end face 180 of the terminating member 128 and a one of the first and second side wall 44, 46 have a slot 160 provided therein. As can be seen in FIG. 11, and in the embodiment described herein, this slot 160 extends from a central region of the end face 180 towards the second wall 146 and then continues in an orthogonal direction along substantially the whole length of the second wall 146, thereby defining the slot 160 which extends from the end face 180 and down one side of the terminating member 128. In an alternative, the slot 160 could extend down the other side of the terminating member 128.

The linkage and connection arrangement of the second lever arm 122 is provided at one of end of a handle 132 and comprises an extension plate 134 with an arm 158 extending substantially perpendicular thereto and a return flange 182 defining a U-shaped recess 196 arranged to receive the projection 148 therein. The pair of aligned holes 154 is provided in the U-shaped recess.

The linkage and connection arrangement also includes an arcuate grooved portion 164 extending in the opposite direction to the extension plate 134. The arcuate grooved portion 164 is formed to retain a linkage arm 166 therein, the linkage arm 166 having a circular-shaped end portion 170 for cooperation with, and retention in, the arcuate grooved portion 164, for example through snap fit retention. In this way, the linkage arm 166 is pivotable with respect to the grooved portion 164.

The linkage arm 166 has a second arcuate groove 168 at its other end, formed to retain the free end of a control arm 142 of a gripping member in the form of a jaw component 150, for example using a snap fit, for relative pivotable movement therewith.

As with the first embodiment described above, the jaw component 150 is located in the circular cavity 126, and can be rotated within the circular cavity 126 to cause a pin, such as one of the fixation pins 16, whose end is received into the circular cavity 126 to be gripped when the second lever arm 122 is moved relative to the first lever arm 120.

The terminating member 128 is held in place for relative slidable movement against the elongate body part 124 by connection of the projection 148 to the extension plate 134 of the connection and linkage arrangement of the second lever aim 122. Similarly, the jaw component 150 is retained in place by means of the terminating member 128, and the linked connection of the jaw component 150 to the second lever arm 122 via the linkage arm 166.

The terminating member 128 can slide relative to the body part 124 of the first lever arm 120, in a direction towards the substrate from which the pin 16 is to be extracted. In the context of the application described above, the substrate can be the femur 2.

The jaw component 150 has a jaw component channel 172 extending through it. The jaw component channel 172 has a similar cross-sectional size and shape as the elongate cavity 138 and is formed so that, when the jaw component 150 is in place in the circular cavity 126, the jaw component channel 172 can align with the elongate cavity 138 to define a channel 194 into which the free end of the fixation pin 16 can be received.

The slot 160 is formed in the terminating member 128 so as to be in alignment with the channel 194. In this way, the slot 160 aligns with the channel 194 formed by the elongate cavity 138 and the jaw component channel 172 so that a fixation pin 16 can be inserted into the instrument 110 either directly forwards through the portion of the slot 160 in the end face 180 of the terminating member 128 or sideways via the portion of the slot 160 provided in the limb 146. Unlike the first embodiment, the surgeon is not required to necessarily use any forward movement to ensure that the fixation pin 16 is located into the jaw component 150: a simple sideways entry into the elongate body part 124 can be used.

The construction and assembly of the second embodiment is differs somewhat from the first embodiment so as to avoid the use of welding and extra components (such as axles 58, 86). The parts of the second embodiment have been designed with a plurality of interlocking parts (similar to a jigsaw puzzle), which allows the tie-bar/linkage piece 166 to assemble into the two levers only when the two levers are in an extreme position, beyond that accessible in normal use. The linkage part is then captured by virtue of the fact that one of its dog-leg portions 170 is contained within a large slot 164 on the moving lever 122. Hence, the instrument can be assembled from the interlinking parts together in a loose chain, until finally the spigots 152 are fitted into aligned holes 154 to complete assembly of the instrument.

Operation of the instrument 110 is similar to the first embodiment.

The fixation pin 16 is inserted into the instrument 110 either through the portion of the slot 160 in the end face 80 of the terminating member 128 or in a sideways movement utilising the portion of the slot 160 provided at the side of the terminating member 128 in the limb 146.

As with the first embodiment, relative movement between the first and second lever arms 120, 122 initially causes the jaw component 150 within the elongate body part 124 to be actuated from an unlocked position to a locked position so that the inserted pin 26 is gripped by the jaw component.

Continued movement of the second lever arm 122 relative to the first lever arm 120 causes the terminating member 128 to slide towards the substrate and away from the elongate body part 124, so that the inserted pin 16 which is gripped by the jaw component 150 is displaced relative to the substrate.

As with the first embodiment, the circular jaw component 150 is a close fit in the circular cavity 126, and is dimensioned so that it can rotate without excessive play in contact within the circular cavity 126.

Squeezing the first and second lever arms 120, 122 together causes the control arm 142 to be drawn back away from the substrate from which the pin 16 is to be extracted. This, in turn, causes the jaw component 150 to rotate within the circular aperture 126 in the elongate body part 124. As the jaw component 150 rotates within the cylindrical cavity 26, portions of the inner surfaces at the ends of the channel 172 impart a shearing action to the fixation pin 16, as a result of applying a localised bending force to the pin. This causes the fixation pin 16 to be gripped within the instrument 110, resisting sliding of the fixation pin 16 in and out of the instrument 110.

Continued squeezing together of the first and second lever arms 120, 122 causes the extension plate 134 and thus the projection 148 coupled thereto to move forward which moves the terminating member 128 forward relative to the elongate body part 124. Accordingly, squeezing together of the first and second lever arms 120, 122 causes the terminating member 128 to be thrust forward relative to the body part 124 of the first lever arm 120.

The result of the continued squeezing together of the first and second lever arms 120, 122 and consequential movement of the terminating member 128 will cause the fixation pin 16 to be extracted at least partially from the bone or other substrate. Partial extraction using the instruments of the present invention will often be sufficient to loosen the fixation pin 16 so that it can then be slid out of the substrate completely. If the fixation pin 16 has not been loosened sufficiently to enable it to be extracted completely, other than with the application of significant pulling force, the first and second lever arms can be opened, and, while the end of the instrument remains in contact with the bone, the rest of the instrument can be slid along the fixation pin 16. The first and second lever arms 120, 122 can then be squeezed together to repeat the sequence which has been described above.

The instrument of the invention can be used to extract various types of non-threaded fixings. For example, the invention can be used to extract various types of pins such as "Steinmann pins" which are similar to nails. The instrument can also be used to extract "drill pins" which appear very much like a drill bit but can be hammered into the bone. However, the invention is not intended to be used to extract "threaded pins" which look like screws (and come in headed and non-headed varieties). However, in very soft bone or with a really strong grasp it may be possible to extract threaded pins too but there is the risk of pulling out a large piece of bone with the pin.

The diameter range of the pins that each embodiment will accept is limited to some extent by the size of the slots and apertures (and is a pin diameter of about 3 mm for the illustrated embodiments). However, it will be appreciated that greater and lesser diameter pins can be accommodated by changing the size of the instrument parts accordingly. The instrument can also be used to extract long and very long pins, such as k-wires. In particular, the second embodiment has particular advantages when being used to extract long or very long pins or wires.

Modifications are possible within the scope of the present invention.

Either or each of the channels in the body part and the jaw component can have a variety of shapes and profiles, for example, partially open in the form of a trough or groove, or closed in the form of a bore. Dimensions should preferably be chosen so that the fixation pin is a close sliding fit.

The instrument will generally be made from one or more biocompatible materials. The choice of suitable materials will be made having regard to the intended application of the instrument. When the instrument is intended for use in surgery, for example in orthopaedic surgery, it will generally be preferred for the instrument to be made from stainless steels such as are commonly used in the manufacture of surgical instruments.

Other biasing structures could be used rather than leaf springs or coiled springs. The shapes of the lever arms can be adapted to suit the particular use of the instrument.

The invention claimed is:

1. An instrument for extracting a pin from a substrate, the instrument comprising:
   a first lever arm with a body part having a channel in which a free end of a pin can be received,
   a second lever arm which can pivot relative to the first lever arm, a gripping member within the body part by which the pin can be gripped to retain the pin in the channel, and a terminating member mounted on the body part having an end face and two side walls which extend along opposite sides of the body part, wherein the terminating member has a slot provided in a portion of the end face and extending along a portion of at least one of the two side walls, the slot configured to guide the free end of the pin into the instrument prior to being received into the channel;

wherein the body part includes a main section and a tip portion having a forward face with an aperture provided in the forward face for guiding the pin into the channel, and the terminating member includes an inclined, recessed guide surface for guiding the free end of the pin into alignment with the aperture.

2. The instrument of claim 1, wherein the body part includes a main portion with the channel therein and the slot is provided along the length of the at least one side wall and aligned to the channel such that the pin can be received into the channel sideways through the slot.

3. The instrument of claim 1, wherein the slot has a stop surface for limiting lateral movement along the end face of the terminating member.

4. The instrument of claim 1, wherein the first lever arm is inclined with respect the body part.

5. The instrument of claim 1, wherein the terminating member is configured to slide relative to the body part in a direction towards the substrate in response to relative movement of the first lever arm and the second lever arm to so that the pin when gripped by the gripping member is displaced relative to the substrate.

6. The instrument of claim 1, wherein the first lever arm is inclined to the body part.

7. The instrument of claim 1, including a biasing member connected to the first and second lever arms to bias the first and second lever arms to an open position.

8. The instrument of claim 1, wherein the instrument comprises entirely a plurality of inter-locking parts which can be assembled into the instrument without using any ancillary parts.

9. The instrument of claim 1, wherein the first and the second lever arm each include protuberances toward a leading end and a trailing end of a handle part of each lever arm.

10. An instrument for extracting a pin from a substrate, the instrument comprising:

a first lever arm with a body part having a channel in which a free end of a pin can be received, a second lever arm which can pivot relative to the first lever arm, a gripping member within the body part by which the pin can be gripped to retain the pin in the channel, and a terminating member mounted on the body part having an end face and two side walls which extend along opposite sides of the body part, wherein the terminating member has a slot provided in a portion of the end face and extending along a portion of at least one of the two side walls, the slot configured to guide the free end of the pin into the instrument prior to being received into the channel;

linkage members connected to the second lever arm and the gripping member such that relative movement of the first lever arm and second lever arm causes the gripping member to grip the pin.

* * * * *